US006551622B1

(12) United States Patent
Jackson

(10) Patent No.: US 6,551,622 B1
(45) Date of Patent: Apr. 22, 2003

(54) DRY POWDER COMPOSITIONS

(75) Inventor: Peter Jackson, Cambridge (GB)

(73) Assignee: Quadrant Holdings Cambridge, Ltd (GB)

( * ) Notice: Subject to any disclaimer, the term of this patent is extended or adjusted under 35 U.S.C. 154(b) by 0 days.

(21) Appl. No.: 09/614,233

(22) Filed: Jul. 12, 2000

(30) Foreign Application Priority Data

Jul. 12, 1999 (GB) .............................................. 9916316

(51) Int. Cl.[7] .......................... A61K 9/50; A61K 38/00
(52) U.S. Cl. ......................... 424/499; 514/2; 424/488; 424/489; 424/493
(58) Field of Search ................... 514/2, 49; 435/320.1, 435/325, 455, 458; 424/458, 450, 488, 489, 499

(56) References Cited

U.S. PATENT DOCUMENTS

| 4,880,635 A | * | 11/1989 | Janoff et al. ................ 424/450 |
| 5,407,914 A | * | 4/1995 | Cochrane et al. ............. 514/11 |
| 5,674,980 A | * | 10/1997 | Frankel et al. .............. 530/350 |
| 5,811,406 A | * | 9/1998 | Szoka, Jr. et al. ............ 514/44 |
| 5,952,008 A | * | 9/1999 | Blackstrom et al. ........ 424/499 |
| 5,955,448 A | | 9/1999 | Colaco et al. |
| 5,958,455 A | | 9/1999 | Roser et al. |
| 5,994,314 A | * | 11/1999 | Eljamal et al. ................ 514/44 |
| 5,997,848 A | * | 12/1999 | Patton et al. .................. 424/43 |
| 6,034,080 A | | 3/2000 | Colaco et al. |
| 6,093,816 A | * | 7/2000 | Lin et al. ..................... 544/122 |
| 6,352,722 B1 | | 3/2002 | Blair |
| 2001/0038858 A1 | | 11/2001 | Roser et al. |

FOREIGN PATENT DOCUMENTS

| WO | 9603978 | | 8/1995 |
| WO | 96/27393 | * | 9/1996 |
| WO | WO 98/29097 A | | 7/1998 |
| WO | 9901463 | | 7/1998 |
| WO | WO 99/33853 A | | 7/1999 |

OTHER PUBLICATIONS

Anderson et al., Human gene therapy, Apr. 30, 1998, Nature, vol. 392, pp. 25–30.*

Verma et al., Gene therapy–promises, problems and propects, Sep. 18, 1997, Nature, vol. 389, pp. 239–242.*

* cited by examiner

*Primary Examiner*—Dave T. Nguyen
(74) *Attorney, Agent, or Firm*—Saliwanchik, Lloyd & Saliwanchik

(57) ABSTRACT

A hydrophilic therapeutic agent is prepared in storage-stable form, suitable for administration to a patient. The agent is formulated with a hydrophobically-derivatized carbohydrate, making use of ion-pair formation to form a solution of the agent and carbohydrate.

21 Claims, No Drawings

DRY POWDER COMPOSITIONS

This application claims foreign priority benefits to GB 9916316.4, filed Jul. 12, 1999.

FIELD OF THE INVENTION

This invention relates to the production of stabilised therapeutic agents, prepared using hydrophobically-derivatised carbohydrates, and to therapeutic compositions.

BACKGROUND OF THE INVENTION

Numerous therapeutic proteins and peptides are currently available for clinical use. A variety of delivery methods and routes exist, of which the parenteral route is the most widely used. Delivery via the pulmonary route is an attractive alternative mainly due to acceptability by patients. There is also evidence to suggest that relatively large molecules such as proteins can be absorbed readily across the lung surface and into the blood stream. Techniques for pulmonary delivery are still in the early stages of development, and as a result, considerable scope or new pulmonary, formulations of therapeutic proteins and peptides exists.

One way of formulating therapeutic proteins is by the use of carbohydrates, which act to stabilise the proteins during storage and also aid delivery. An example of a stabilising carbohydrate is trehalose.

Recently, there has been interest in using hydrophobically-derivatised carbohydrates (HDCS) in formulating proteins. WO-A-96/03978 discloses compositions comprising a HDC and therapeutic agent, formulated into solid dose form for direct delivery. The compositions may be powders for pulmonary delivery, microneedles or microparticles for ballistic, transdermal delivery or implantable compositions.

The advantage in having a therapeutic agent formulated with a HDC, is that there is the potential for developing controlled release delivery systems. In addition, the HDC may itself have desirable properties that aid delivery, in particular to the deep lung.

However, therapeutic proteins are generally hydrophilic, and due to the hydrophobicity of HDC molecules, the incorporation of proteins into HDCs is problematic.

There is therefore a need for an efficient process by which hydrophilic agents can be incorporated into HDCs.

SUMMARY OF THE INVENTION

The present invention is based on the realisation that hydrophilic agents can be incorporated efficiently into HDCs by the use of hydrophobic ion-pairing (HIP).

According to a first aspect of the present invention, a method for the preparation of a therapeutic composition, comprises forming a solution, in an organic solvent, of a hydrophobically-derivatised carbohydrate and an ion-pair complex of a hydrophilic therapeutic agent and an ionic substance; and drying the solution.

In one embodiment, the method comprises the steps of:
(i) mixing the therapeutic agent with the ionic substance, in an aqueous medium, to form a precipitate;
(ii) dissolving the precipitate and the HDC in an organic solvent; and
(iii) drying the resulting organic solution.

In a further embodiment, the method comprises the steps of:
(i) mixing the therapeutic agent in aqueous solution with the ionic substance to form the ion-pair complex;
(ii) adding a water-immiscible organic solvent to form an organic phase, and allowing the ion-pair complex to pass into the organic phase;
(iii) separating the organic phase;
(iv) adding the HDC to the organic phase; and
(v) drying the resulting organic solution.

According to a second aspect, a composition comprises, in solid dose form, a hydrophobically-derivatised carbohydrate, a therapeutic agent and a pharmaceutically acceptable ionic detergent.

According to a third aspect, compositions of the invention may be used in the manufacture of a medicament to be administered to a patient via the pulmonary route, for the treatment of a disease.

The products are intended for therapeutic use, and the active agent will be therapeutically active on delivery.

The effective incorporation of a hydrophilic agent into the HDC provides useful therapeutics to be formulated with desirable controlled release properties.

DESCRIPTION OF THE INVENTION

The method according to the present invention is based on the realisation that hydrophobic ion-pairing is a useful method applicable to formulating a hydrophilic agent with a hydrophobic carbohydrate.

In summary, the procedure involves generating hydrophobic ion-pairs between positive charges on the actives, e.g. proteins, and negative charges on selected anionic surfactants. Alternatively, the polarity of the charges on the protein and surfactant can be reversed.

The present method may be carried out under conditions known so those skilled in the art. It is well known that hydrophilic proteins can be precipitated out of solution using low concentrations of an anionic detergent. It appears that precipitation is the result of displacement by the detergent of counter-ions from the ion-pairs on the protein. The precipitate may then be isolated by, for example, centrifugation, and then subsequently dissolved in an organic solvent containing the HDC. The hydrophilic agent is then in solution with the HDC and can be dried to form a solid. The total recovery of the active is high, and consequently, the present method offers a commercial scale process to be developed.

Alternatively, the ion-pair may be formed without a precipitate, by phase separation. A protein in an aqueous phase is mixed with a suitable detergent to form an ion-pair. A suitable organic solvent is added to form an organic phase, and the ion-pair complex is allowed to incorporate into the organic phase. The organic phase may then be separated and mixed with the HDC, optionally comprised within a further organic solvent.

Hydrophilic Agents

The hydrophilic agents that may be used in the present invention include any therapeutically active protein, peptide, polynucleotide or ionic drug. In particular, the agent may be an enzyme or a hormone, Examples include, but are not limited to, insulin, interferons, growth factors, α-chymotrypsin interleukins, calcitonin, growth hormones, leuprolide, colony-stimulating factors and DNase. Insulin is a preferred embodiment, and is a desirable therapeutic is for pulmonary delivery.

Ionic Substances

Any suitable ionic substance may be used in the invention. A preferred substance is a detergent. The substance is preferably anionic when proteins or peptides are to be incorporated into the HDCs. When polynucleotides or negatively charged proteins are the active agent, the substance should preferably be cationic. Suitable anionic substances include salts, e.g. sulphates, sulphonates, phosphates and carboxylates.

Examples of suitable anionic detergents include sodium dodocyl sulphate (SDS), sodium docusate (AOT), phosphatidylinositol (PPI), 1,2-dipalmitoyl-sn-glycero-3-phosphatidic acid sodium salt (DPPA.Na), 1,2-dipalmitoyl-sn-glycero-3-phosphoglycerol sodium salt (DPPG.Na) and sodium oleate. Examples of suitable cationic detergents include benzalkonium chloride (BAC), hexadecyltrimethylammonium bromide (CTAB) and dodecyltrimethylammonium bromide (DoTAB).

Preferably, the detergent should be pharmaceutically acceptable. In particular, the detergent should be suitable for pulmonary delivery.

Organic Solvents

Any suitable organic solvent may be used in the present invention. Polar or non-polar solvents may be used depending on the active agent. In general, the solvent will be one that is pharmaceutically acceptable. Suitable solvents include, but are not limited to, ethanol, propanol, isopropanol, 1-octanol, acetone, ether, ethyl acetate, ethyl formate, dichloromethane (DCM), hexane and methanol.

Hydrophobically-derivatised Carbohydrates (HDCs)

The HDC may be any of those known in the art. Preferably, the HDC forms an amorphous glass with a high Tg, on drying.

Preferably, the HDC is capable of forming a glass with a Tg greater than 20° C., more preferably greater than 30° C., and most preferably greater than 40° C.

As used herein, "HDC" refers to a wide variety of hydrophobically-derivatised carbohydrates where at least one hydroxyl group is substituted with a hydrophobic moiety including, but not limited to, esters and ethers.

Numerous examples of suitable HDCs are described in WO-A-96/03978 and WO-A-99/01463. Specific examples of HDCs include, but are not limited to, sorbitol hexaacetate (SHAC), α-glucose pentaacetate (α-GPAC), β-glucose pentaacetate (β-GPAC), 1-O-octyl-β-D-glucose tetraacetate (OGTA), trehalose octaacetate (TOAC), trehalose octapropanoate (TOPR), β-4',6'-diisobutyroyl hexaacetyl lactose, sucrose octaacetate (SOAC), cellobiose octaacetate (COAC), raffinose undecaacetace (RUDA), sucrose octapropanoate, cellobiose octapropanoate, raffinose undecapropanoate, tetra-O-methyl trehalose, di-O-methyl-hexa-O-acetyl sucrose, and trehalose 6,6-diisobutyrate hexaacetate.

Pure single HDC glasses have been found to be stable at ambient temperatures and up to at least 60% humidity. Mixtures of HDC glasses incorporating certain active substances are, however, surprisingly stable at ambient temperatures and up to at least 95% humidity. Mixtures of different HDCs may be desirable, to achieve differing controlled release profiles.

Many factors influence the extraction of proteins into organic solutions, namely, buffer pH and ionic strength, protein molecular weight, detergent: protein ratios, pI and distribution of charge, as well as surfactant properties and solvent properties. Variation of these parameters may be required to maximise the efficiency of the method steps. This will be apparent to a skilled person.

The parameters may also be varied to achieve differing controlled release properties for the resulting products. For example, the HIP complex:HDC ratio or variations in solvent blends may influence the release properties. Variations in these parameters will also be apparent to the skilled person.

The formulations may be dried by any suitable method, including freeze-drying, oven drying, supercritical fluid processing and, preferably, spray-drying. Spray-drying is preferred as it allows very rapid evaporation of solvent, leaving a glassy amorphous product with low residual solvent level. The glassy amorphous product should preferably be stable at room temperature, or above, to allow easy storage of the compositions without losses in activity.

The dried product should preferably be in a solid form which is storage stable at room temperature, or above. The stability may be attributable to the carbohydrate which forms a glassy amorphous structure on drying. In one embodiment, the product has a glass transition temperature (Tg) above 20° C., preferably above 30° C. The product may be in a solid form suitable for direct delivery to a patient. Preferably, the product is a dry powder or "microspheren" having a diameter of less than 30 µm, preferably less than 10 µm and most preferably less than 5 µm. These powders are suitable for pulmonary delivery. The product may also be a microneedle for ballistic or transdermal delivery.

The following Examples illustrate the invention.

EXAMPLE 1

α-Chymotrypsin (CMT)

α-Chymotrypsin (CMT) is a non-membrane-associated protein which has a pI of 8.5 and a net positive charge between pH 5 and 6. Efficient partitioning of CMT into organic solvent has been achieved when CMT was mixed with 40 equivalents of sodium docusate in 10 mM potassium acetate/$CaCl_2$ buffer at pH 5. It was also noted that ionic strength played a very important role in the efficiency of extraction, mainly through control of the formation of emulsions. The ionic strength was controlled by varying the calcium chloride concentration and a general trend emerged, which showed that a decrease in ionic strength resulted in a drop in the percentage recovery of protein into solvent. The choice of organic solvent is important as it has been found, using CD measurements, that CMT was native-like in non-polar solvents such as isooctane, declain and carbon tetrachloride but had little or no organised structure in more polar solvents such as dichloromethane.

CMT at a concentration of 2 mg/ml in 10 mM sodium acetate, 5 mM calcium chloride, pH 7.0, was mixed with 50 molar equivalents of AOT at a concentration of 1.778 mg/ml in hexane, Following centrifugation, the organic layer was isolated, dried in vacuo and the protein concentration determined using the BCA assay. Calculations showed that 80–90% of the enzyme was extracted into the solvent.

This experiment was then repeated with TOAC being present in an organic solvent. TOAC (60 mg/ml in acetone) was added to the HIP sample of CMT (2 mg/ml in hexane) resulting in a final composition of 30 mg/ml TOAC and 1 mg/ml CMT in acetone and hexane (1:1). The amount of TOAC used was between 5 and 10 times the amount of enzyme. The resulting solution was spray-dried to form a dry powder composition.

EXAMPLE 2

Insulin (i) Insulin (5 mg/ml) in 10 mM sodium acetate buffer, pH 2.5, was mixed with 4.5 molar equivalents of AOT (10 mg/ml) in water, resulting in efficient precipitation of the protein. The protein was isolated by centrifugation and the resultant pellet re-dissolved in a mixture of acetone and IPA (1:2) containing 25 mg/ml TOAC or TIBAC. BCA analysis of the dried mixture showed 99% of the protein was recovered in the solvent. Spray-drying the solution gave yields up to 43% and early analysis of the spray-dried material by DSC indicated the presence of a glass.

(ii) Insulin was hydrophobically ion-paired with 7.5 molar equivalents of benzalkonium chloride in 10 mM sodium carbonate buffer, pH 11, and redissolved in acetone and IPA (1:2) containing 25 mg/ml TOAC. BCA analysis of this formulation revealed 92% of the protein was extracted into solvent. Spray-drying of this formulation resulted in 18% recovery.

(iii) Insulin was also spiked with 2% FITC-labelled insulin, extracted into IPA and acetone (ratio 2:1) containing TOAC using AOT, and spray-dried. The percentage of protein recovered in the solvent was 96%, and spray, drying gave a 35% recovery of material.

EXAMPLE 3

α-L-phosphatidylinositol (PPI)

An initial experiment was performed to investigate the optimum amount of PPI required to yield a high recovery of insulin into organic solvent. The amount of PPI was varied from 5 to 7.5 molar equivalents for 2 mg samples of insulin. The insulin was dissolved in 10 mM sodium acetate buffer, pH 2.5 (2 mg/ml), and a solution of 5 mg/ml PPI was prepared in water. Precipitation occurred on addition of PPI to each insulin sample and the precipitates were collected by centrifugation at 2500 rpm for 2 minutes. The pellets were resuspended in a variety of different solvents, i.e. acetone, dichloromethane, ethanol and mixtures of these. A 90% recovery in the organic solvent was achieved when dichloromethane and ethanol (ratio 1:1) was employed. The precipitate readily dissolved to give a 2 mg/ml solution.

EXAMPLE 4

Insulin with DPPA, DPPG

Two lecithin derivatives were examined as potential surfactants for the HIP of insulin. Standard buffer conditions were used (10 mM sodium acetate buffer, pH 2.5) throughout. Optimisation of the conditions required to HIP insulin with DPPA.Na involved varying the molar equivalents of the surfactant from 5 up to 20. The precipitates were dissolved in ethanol:DCM (1:1) and a recovery of 71% was achieved when 9 molar equivalents were used.

The second lecithin derivative to be examined was DPPG.Na. Again, the reaction conditions were optimised by varying the quantity of DPPG added relative to insulin. The quantities investigated ranged from 5 to 12 molar equivalents. Following analysis by the BCA assay, approximately 88% of the protein was recovered in the organic solvent when 8 molar equivalents were used.

EXAMPLE 5

Leuprolide

In an attempt to broaden the application of HIP, additional rest molecules were investigated. The LHRH analogue leuprolide acetate has two possible rices for HIP. Initial experimentation compared the reaction in 10 mM sodium acetate buffer, pH 2.5, and 100 mM sodium citrate buffer, pH 5. PPI was used as the surfactant, and the addition of 2 molar equivalents resulted in a clear, sticky pellet forming in the sample conducted in acetate buffer. BCA analysis of the pellet resuspended in ethanol:DCM (1:1) revealed 66% of the peptide had been recovered in the acetate sample whilst only 3% was recovered at pH5. A standard curve for the BCA assay using leuprolide was constructed and the reaction repeated. Between 63 and 66% recovery was obtained.

The reaction was also attempted with DPPG.Na. The buffer was kept as 10 mM sodium acetate, pH 2.5. Owing to the insolubility of DPPG.Na in water compared with PPI, a range of molar equivalents was examined. The amount of DPPG.Na was varied between 1 and 5 times the amount of peptide. The results indicated that an increase in the amount of DPPG.Na resulted in an increase in percentage recovery of the peptide. The highest recovery (65%) was achieved when 5 molar equivalents were used.

EXAMPLE 6

Trypsin

Trypsin was also investigated, as an example of an enzyme. The aim was to demonstrate that activity can be maintained following HIP. 2 mg/ml trypsin in 10 mM sodium acetate buffer, pH 2.5, was mixed with varying molar equivalents of DPPG (from 40× to 100×) and the precipitates collected. Resuspension in ethanol:DCM (1:1) and subsequent analysis by the BCA assay showed the recoveries ranged from 72% to 83%. The precipitates formed with 90 and 100 equivalents of DPPG were not very soluble in solvent, probably due to the amount of lecithin present. Further optimisation with 60 molar equivalents of DPPG was attempted.

A further reaction investigated varying the pH of the acetate buffer from pH 2.5 up to pH 7.3. The best recovery was obtained at pH 2.5. The amount of enzyme taken up into the organic solvent was 74%. Finally, the initial concentration of the enzyme was increased from the standard 2 mg/ml to 5 and 10 mg/ml. BCA analysis of the redissolved pellets showed approximately 86% had been recovered when the initial enzyme concentration was 5 mg/ml.

I claim:

1. A method for the preparation of a therapeutic composition, comprising forming a solution, in an organic solvent, of a hydrophobically-derivatized carbohydrate (HDC) and an ion-pair complex of a hydrophilic therapeutic protein or peptide and an ionic substrate; and drying the solution wherein said method comprises the steps of:

(i) mixing the therapeutic protein or peptide in aqueous solution with the ionic substance to form the ion-pair complex;

(ii) adding a water-immiscible organic solvent to form an organic phase, and allowing the ion-pair complex to pass into the organic phase;

(iii) separating the organic phase;

(iv) adding the HDC to the organic phase; and (v) drying the organic solution.

2. A method for the preparation of a therapeutic composition, comprising forming a solution, in an organic solvent, of a hydrophobically-derivatized carbohydrate (HDC) and an ion-pair complex of a hydrophilic therapeutic protein or peptide and an ionic substrate; and drying the solution wherein said method comprises the steps of:

(i) mixing the therapeutic protein or peptide with the ionic substance in an aqueous medium, to form a precipitate;

(ii) dissolving the precipitate and the HDC in an organic solvent; and (iii) drying the solution.

3. The method, according to claim 2, wherein the precipitate is isolated prior to step (ii).

4. The method, according to claim 1, wherein the therapeutic protein or peptide is an enzyme or hormone.

5. The method, according to claim 1, wherein the therapeutic protein or peptide is insulin.

6. The method, according to claim 1, wherein the HDC has a carbohydrate backbone and at least one hydroxyl group substituted with a less hydrophilic derivative thereof.

7. The method, according to claim 1, wherein the HDC is selected from the group consisting of sorbitol hexacetate, α-glucose pentaacetate, β-glucose pentaacetate, 1-0-octyl-β-D-glucose tetraacetrate, trehalose octaacetate, trehalose octapropanoate, sucrose octaacetrate, β-4', 6'-diisobutyroyl hexaacetyl lactose, sucrose octapropanoate, cellobiose octaacetate, raffinose undecaacetate, raffinose undecapropanoate and trehaloe 6,6-diisobutyrate hexaccetate.

8. The method, according to claim 1, wherein drying is carried out by spray-drying.

9. The method, according to claim 1, wherein the ionic substance is a detergent.

10. A composition, comprising, in solid dose form, a hydrophobically-derivatized carbohydrate, and an ion-pair complex formed between a hydrophilic therapeutic protein or peptide and a pharmaceutically acceptable ionic substrate; wherein the solid dose form is particles having a size of less than 10 μm.

11. The composition, according to claim 10, obtainable by a method comprising forming a solution, in an organic solvent, of a hydrophobically-derivatized carbohydrate (HDC) and an ion-pair complex of a hydrophilic therapeutic agent and an ionic substance; and drying the solution.

12. The composition, according to claim 10, wherein the composition is in a glassy, amorphous form having a Tg above 20° C.

13. The composition, according to claim 10, wherein the solid dose form is microneedles suitable for ballistic delivery.

14. A method for delivering a hydrophilic therapeutic protein or peptide to a mammal wherein said method comprises administering to said mammal the composition of claim 10.

15. A device for the pulmonary delivery of a hydrophilic therapeutic protein or peptide, wherein the device includes a composition comprising, in solid dose form, a hydrophobically-derivatized carbohydrate, the hydrophilic therapeutic protein or peptide, and a pharmaceutically acceptable ionic detergent, wherein the solid dose form is particles having a size of less than 10 μm.

16. The method, according to claim 2, wherein the therapeutic protein or peptide is an enzyme or hormone.

17. The method, according to claim 2, wherein the therapeutic protein or peptide is insulin.

18. The method, according to claim 2, wherein the HDC has a carbohydrate backbone and at least one droxyl group substituted with a less hydrophilic derivative thereof.

19. The method, according to claim 2, wherein the HDC is selected from the group consisting of sorbitol hexacetate, α-glucose pentaacetate, β-glucose pentaacetate, 1-0-octyl-β-D-glucose tetraacetrate, trehalose octaacetate, trehalose octapropanoate, sucrose octaacetrate, β-4', 6'-diisobutroyl hexaacetyl lactose, sucrose octapropanoate, cellobiose octaacetate, raffinose undecaacetate, raffinose undecapropanoate and trehaloe 6,6-diisobutyrate hexaccetate.

20. The method, according to claim 2, wherein drying is carried out by spray-drying.

21. The method, according to claim 2, wherein the ionic substance is a detergent.

* * * * *

UNITED STATES PATENT AND TRADEMARK OFFICE
CERTIFICATE OF CORRECTION

PATENT NO.   : 6,551,622 B1
DATED        : April 22, 2003
INVENTOR(S)  : Peter Jackson It is certified that error appears in the above-identified patent and that said Letters Patent is hereby corrected as shown below:

<u>Column 8,</u>
Line 22, "at least one droxyl group" should read -- at least one hydroxyl group --.

Signed and Sealed this

Twenty-third Day of March, 2004

JON W. DUDAS
*Acting Director of the United States Patent and Trademark Office*